US008562946B2

(12) United States Patent
Lacy

(10) Patent No.: US 8,562,946 B2
(45) Date of Patent: *Oct. 22, 2013

(54) MINIATURIZED $^{62}$ZN/$^{62}$CU GENERATOR FOR HIGH CONCENTRATION CLINICAL DELIVERY OF $^{62}$CU KIT FORMULATION FOR THE FACILE PREPARATION OF RADIOLABELED CU-BIS(THIOSEMICARBAZONE) COMPOUNDS

(75) Inventor: Jeffrey L. Lacy, Houston, TX (US)

(73) Assignee: Proportional Technologies, Inc., Houston, TX (US)

( * ) Notice: Subject to any disclaimer, the term of this patent is extended or adjusted under 35 U.S.C. 154(b) by 17 days.

This patent is subject to a terminal disclaimer.

(21) Appl. No.: 13/234,784

(22) Filed: Sep. 16, 2011

(65) Prior Publication Data
US 2013/0064764 A1  Mar. 14, 2013

Related U.S. Application Data

(62) Division of application No. 10/571,202, filed as application No. PCT/US2004/029252 on Sep. 8, 2004.

(60) Provisional application No. 60/501,156, filed on Sep. 8, 2003.

(51) Int. Cl.
*A61K 51/00* (2006.01)
*A61M 36/14* (2006.01)

(52) U.S. Cl.
USPC ............ 424/1.65; 424/1.11; 424/9.1; 424/9.4

(58) Field of Classification Search
USPC ............ 424/1.11, 1.21, 1.25, 1.29, 1.65, 9.1, 424/1.81, 9.4; 206/223, 569, 570
See application file for complete search history.

(56) References Cited

U.S. PATENT DOCUMENTS

| 5,573,747 A | 11/1996 | Lacy |
| 2003/0017108 A1 | 1/2003 | Zamora et al. |

FOREIGN PATENT DOCUMENTS

| WO | WO 93/12819 | 7/1993 |
| WO | WO 00/18503 | 4/2000 |

OTHER PUBLICATIONS

Robinson et al (International Journal of Applied Radiation and Isotopes, 1980, vol. 31, pp. 111-116).*
Robinson, et al., "The Zinc-62/Copper-62 Generator: A Convenient Source of Copper-62 for Radiopharmaceuticals," International Journal of Applied Radiation and Isotopes, 1980, vol. 31, pp. 111-116.
Fujibayashi, et al., "A New Zinc-62/Copper-62 Generator as a Copper-62 Source for PET Radiopharmaceuticals," The Journal of Nuclear Medicine, 1989, vol. 30, pp. 1838-1842.
Fujibayashi, et al., "Copper-62-ATSM: A New Hypoxia Imaging Agent with High Membrane Permeability and Low Redox Potential," The Journal of Nuclear Medicine, 1977, vol. 38, pp. 1155-1160.
Fujibayashi, et al., "Comparative Studies of Cu-64-ATSM and C-11-Acetate in an Acute Myocardial Infarction Model; Ex Vivo Imaging of Hypoxia in Rats," Nuclear Medicine & Biology, 1999, vol. 26, pp. 117-121.
Zimmerman, et al., "The Standardization of 62 Cu and Experimental Determinations of Dose Calibrator Settings for Generator-Produced 62 CuPTSM," Applied Radiation and Isotopes, 1999, vol. 51, pp. 515-526.
Green, et al., "Copper (II) Bis(thiosemicarbazone) Complexes as Potential Tracers for Evaluation of Cerebral and Myocardial Blood Flow with PET," The Journal of Nuclear Medicine, 1988, vol. 29, pp. 1549-1557.
Green, et al., "Copper-62-Labeled Pyruvaldehyde Bis (N4-methylthiosemicarbazonato) Copper (II): Synthesis and Evaluation as a Positron Emission Tomography Tracer for Cerebral and Myocardial Perfusion," The Journal of Nuclear Medicine, 1990, vol. 31, pp. 1989-1996.
Chervet, et al., "Instrumental Requirements for Nanoscale Liquid Chromatography," Analytical Chemistry, 1996, vol. 68, pp. 1507-1512.
Haynes, et al., "Performance of a 62 Zn/62 Cu Generator in Clinical Trials of PET Perfusion Agent 62 Cu-PTSM," The Journal of Nuclear Medicine, 2000, vol. 41, pp. 309-314.
Okazawa, et al., "Clinical Application and Quantitative Evaluation of Generator-Produced Copper-62-PTSM as a Brain Perfusion Tracer for PET," The Journal of Nuclear Medicine, 1994, vol. 35, pp. 1910-1915.
Kraus, et al., "Anion Exchange Studies. VI. The Divalent Transition Elements Manganese to Zinc in Hydrochloric Acid," Journal of American Chem. Society, 1952, vol. 75, pp. 1460-1462.
Tadamura, et al., "Generator-Produced Copper-62-PTSM as a Myocardial PET Perfusion Tracer Compared with Nitrogen-13-Ammonia," The Journal of Nuclear Medicine, 1996, vol. 37, pp. 729-735.
Wallhaus, et al., "Copper-62-Pyruvaldehyde Bis(n4-Methyl-Thiosemicarbazone) PET Imaging in the Detection of Coronary Artery Disease in Humans," Journal of Nuclear Cardiology, 2001, pp. 67-74.
Mathias, et al., "Evaluation of a Potential Generator-Produced PET Tracer for Cerebral Perfusion Imaging: Single-Pass Cerebral Extraction Measurements and Imaging with Radiolabeled Cu-PTSM," The Journal of Nuclear Medicine, 1990, vol. 31, pp. 351-359.
Mathias, et al., "Species-Dependent Binding of Copper(II) Bis(Thiosemicarbazone) Radiopharmaceuticals to Serum Albumin," The Journal of Nuclear Medicine, 1995, vol. 36, pp. 1451-1455.
Ackerman, et al., "Synthesis and Evaluation of Copper Radiopharmaceuticals with Mixed Bis(thiosemicarbazone) Ligands," Nuclear Medicine & Biology, 1999, vol. 26, pp. 551-554.

(Continued)

*Primary Examiner* — D L Jones
(74) *Attorney, Agent, or Firm* — Hasley Scarano, LLP

(57) ABSTRACT

A new system accomplishes easy, interchangeable production of multiple PET radiopharmaceuticals through the use of a simplified eluant-only generator and a kit based synthesis technique employing lyophilized or freeze dried ligand. Thus, by simply switching the lyophilized ligand vial kit, any number of $^{62}$Cu-labeled radiopharmaceuticals ($^{62}$Cu-ligand) can be interchangeably synthesized with only one $^{62}$Zn/$^{62}$Cu generator.

20 Claims, 14 Drawing Sheets

(56) References Cited

OTHER PUBLICATIONS

Lewis, et al., "Evaluation of 64 Cu-ATSM in Vitro and in Vivo in a Hypoxic Tumor Model," The Journal of Nuclear Medicine, 1999, vol. 40, pp. 177-183.

Lewis, et al., "Delineation of Hypoxia in Canine Myocardium Using PET and Copper(II)-Diacetyl-bis(N4-Methylthiosemicarbazone)," The Journal of Nuclear Medicine, 2002, vol. 43, pp. 1557-1569.

Lewis, et al., "PET Imaging of Hypoxia," (Abstract), Q.J. Nuclear Medicine, 2001, vol. 45, pp. 183-188.

Dearling, et al., "Copper Bis(thiosemicarbazone) Complexes as Hypoxia Imaging Agents: Structure-Activity Relationships," (Abstract), Journal of Biological Inorganic Chemistry, 2002, vol. 7, pp. 249-259.

Meister, et al., "Glutathione," Ann. Rev. Biochem., 1983, vol. 52, pp. 711-760.

Winkelmann, et al., "Comparative Properties of the Antineoplastic Agent, 3-Ethoxy-2-oxobutyraldehyde Bis (thiosemicarbazonato) Copper(II) and Related Chelates: Linear Free Energy Correlations," Bioinorganic Chemistry, 1974, vol. 3, pp. 261-277.

Petering, et al., "Carcinostatis Copper Complexes," Metal Ions in Biological Systems; Sigel, H., Ed., 1980, vol. 11, pp. 197-229, Marcel Dekker, New York.

Minkel, et al., "Structure-Function Correlations in the Reaction of Bis9thiosemicarbazonato) Copper(II) Complexes with Ehrlich Ascites Tumor Cells," Cancer Research, 1978, vol. 38, pp. 124-129.

\* cited by examiner

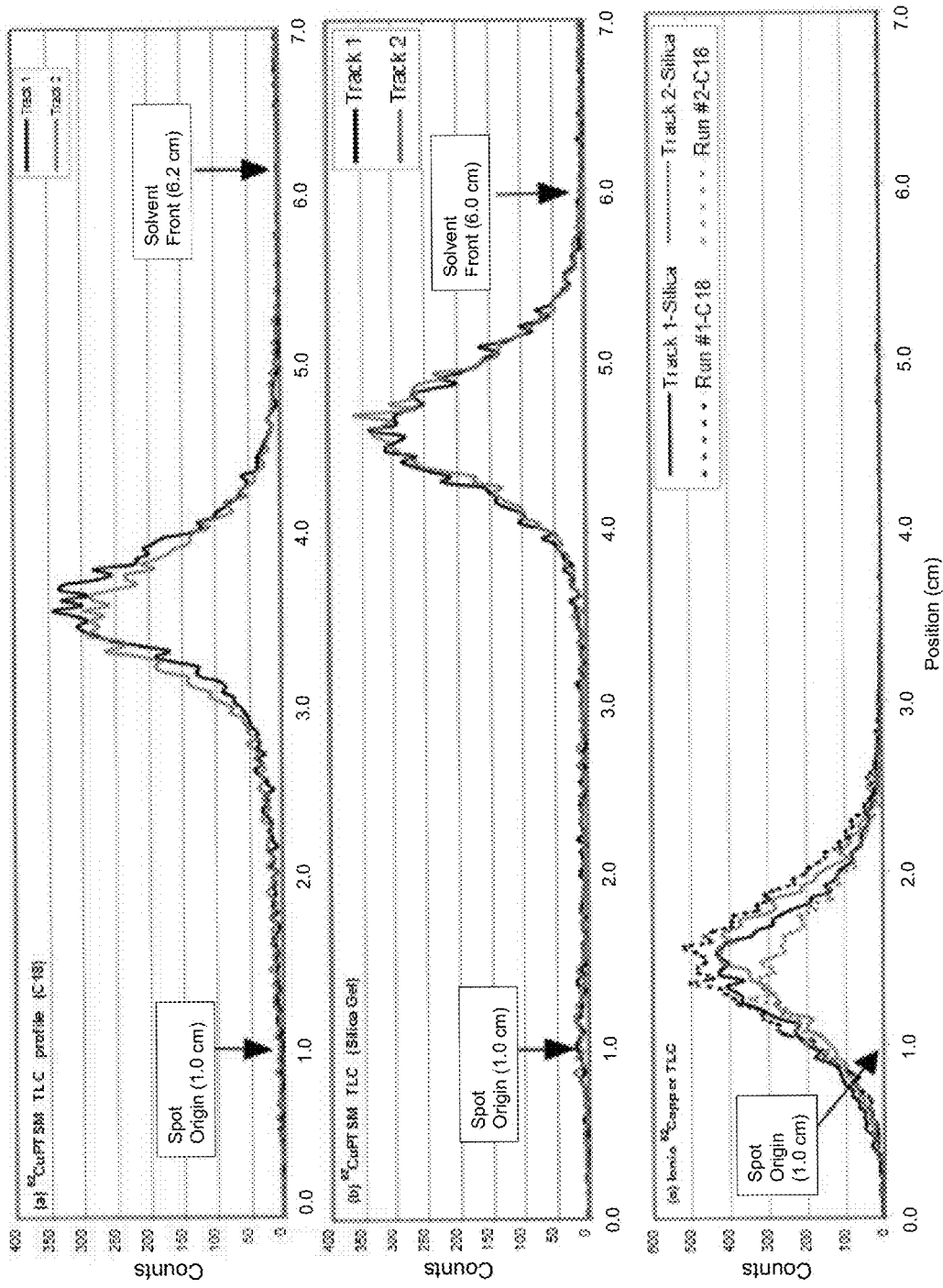
Figure 14 – Replacement Sheet

MINIATURIZED $^{62}$ZN/$^{62}$CU GENERATOR FOR HIGH CONCENTRATION CLINICAL DELIVERY OF $^{62}$CU KIT FORMULATION FOR THE FACILE PREPARATION OF RADIOLABELED CU-BIS(THIOSEMICARBAZONE) COMPOUNDS

This is a divisional application of U.S. patent application Ser. No. 10/571,202 filed Mar. 7, 2006, which is a 371 of PCT/US04/29252 filed Sep. 8, 2004, which claims the benefit of U.S. Provisional Application No. 60/501,156 filed Sep. 8, 2003.

Positron emission tomography (PET) is a highly sensitive imaging technique with many practical advantages over other radionuclide imaging modalities. Traditionally, its widespread clinical application has been limited by the economic burden associated with the purchase, operation, and maintenance of an in-house biomedical cyclotron required to produce the most commonly used short-lived PET radionuclides ($^{15}$O, $^{13}$N, $^{11}$C, and $^{18}$F). Even the well documented advantages of PET are not enough to offset these high expenses. Furthermore, the FDA regulatory issues regarding expedited production of short-lived radioisotopes using in-house cyclotrons are overwhelming.

A significant shift has occurred over the past decade in PET radiopharmaceutical production and distribution. Recognition of the potential of $^{18}$F, which can be produced using small cyclotrons and has a 110-minute half-life long enough for limited distribution, has led to the rise of several commercial PET radiopharmaceutical distribution chains. These efforts have focused on the glucose analog, $^{18}$F-FDG, distributed through regionally located cyclotron equipped pharmacies. Since each of these pharmacies can supply many local clinical facilities, the number of North American PET centers has grown substantially from 230 in 2000 to 603 in 2003. Also the vast majority of facilities now do not have a local cyclotron and rely exclusively on commercially manufactured and distributed $^{18}$F-FDG. Thus, PET has become a one tracer modality and methods of effective distribution of other tracers are lacking.

Substantial laboratory and clinical research suggests that various copper(II) bis(thiosemicarbazone) complexes can be useful as PET agents. A promising example, Copper(II) $^{62}$Cu pyruvaldehyde bis(N4-methylthiosemicarbazone) or $^{62}$Cu-PTSM, has been developed and has demonstrated utility as a myocardial, cerebral, renal, and tumor perfusion agent. This agent has a favorable short half-life of 9.7 minutes that reduces patient radiation dose and allows multiple serial studies during a single brief patient imaging session.

Furthermore, because $^{62}$Cu is produced by a generator based on $^{62}$Zn, with a half life of 9.3 hours, $^{62}$Cu-PTSM can be readily distributed to hospitals through either regional or national distribution systems. Unlike local cyclotron production, regulatory organizations readily embrace distribution through use of a generator.

Another agent in the bis(thiosemicarbazone) family, $^{62}$Cu ethylglyoxal bis(thiosemicarbazone) or $^{62}$Cu-ETS is under investigation in human studies. Similar to $^{62}$Cu-PTSM in structure, $^{62}$Cu-ETS has shown more linear uptake at high blood flow rates and thus may provide a superior PET perfusion tracer for applications such as myocardial perfusion and renal blood flow measurements. Over the past several years, research with another bis(thiosemicarbazone) ligand, diacetyl-bis(N4-methylthiosemicarbazone) or H$_2$ATSM, has revealed that this compound, labeled with copper, has high promise as a hypoxia imaging agent. It has shown heterogeneous uptake in tumors with homogeneous perfusion images, strongly suggesting uptake reflecting hypoxic heterogeneity. Radiolabeled H$_2$ATSM also has produced "hot spot" myocardial images, reflecting hypoxia produced by experimental coronary occlusion. In addition several clinical studies have been reported in which Cu-ATSM tumor hypoxia images have correlated with prognosis and effectiveness of radiotherapy. Thus, $^{62}$Cu-ATSM has the potential to be a very valuable tool by producing PET images which can guide treatment of tumors as well as provide assessment of cardiac and neurological disease. The short 9.7 minute half-life of $^{62}$Cu makes it possible to combine multiple radiopharmaceuticals into one brief clinical imaging procedure. For example use of combined $^{62}$Cu-PTSM imaging of tumor perfusion and tumor hypoxia in closely spaced studies using $^{62}$Cu-ATSM could provide a far more quantitative and accurate evaluation of tumor hypoxia. Finally, $^{62}$Cu radiopharmaceuticals can be distributed much more economically than non-generator produced $^{60}$Cu, $^{61}$Cu, and $^{64}$Cu.

As of now, by far, the largest application of nuclear imaging remains myocardial perfusion imaging in the diagnosis of coronary disease. Such imaging procedures account for more than 50% of all nuclear studies and are performed using single photon imaging which affords much poorer image resolution, less effective attenuation correction, and tracers based on $^{99m}$Tc, which are less capable of tracking blood flow changes in the myocardium during stress. In order to realize the full potential of PET in this field, there is a clear need for distribution methods of tracers other than $^{18}$F-FDG, particularly effective perfusion tracers.

A modular $^{62}$Zn/$^{62}$Cu generator has been developed which produces $^{62}$Cu labeled agents in the bis(thiosemicarbazone) family via a method of in-line synthesis as described in U.S. Pat. No. 5,573,747. The 9.7 minute half-life of $^{62}$Cu is long enough to facilitate radiopharmaceutical synthesis procedures and at the same time, it is short enough that multiple back-to-back imaging procedures are practical during a reasonably brief interval without interference of $^{62}$Cu background activity from a previous injection. Also, such studies can be followed by another agent such as $^{18}$F-FDG after a reasonable delay, on the order of 40 minutes. The ability to perform back to back procedures is extremely beneficial because this is the preferred method of evaluation of myocardial blood flow. Such studies require regional comparison of myocardial uptake at rest with that during pharmacologic or exercise stress. The short half life of $^{62}$Cu offers advantages for such procedures which are currently performed with the 6 hour half-life, $^{99m}$Tc tracer.

The generator produced $^{62}$Cu can be readily distributed to clinical facilities utilizing one of two distribution models. The 9.3 hour half-life $^{62}$Zn parent (which decays to a daughter $^{62}$Cu isotope) can be produced either in or near the $^{18}$F radiopharmacies using a 19 MeV cyclotron. Such a $^{62}$Zn/$^{62}$Cu generator can then be delivered using the same local delivery network already in place for $^{18}$F. Alternatively, the $^{62}$Zn parent can be produced and loaded into generators at a few large centralized facilities using >25 MeV cyclotrons and shipped to the local radiopharmacies or directly to hospitals.

There are many regulatory advantages to using a $^{62}$Zn/$^{62}$Cu generator. Currently, almost all FDA approved radiopharmaceuticals are produced in a central commercial facility under well controlled conditions, and then distributed to local clinics where they are administered. Distribution via a generator system is a well accepted practice and the primary means of distribution of $^{99m}$Tc, which is responsible for the majority of current nuclear medicine practice. Production of radiopharmaceuticals by numerous in-hospital cyclotron facilities is a concept which is not, and may never be, embraced by the FDA in any practical framework. In contrast, radionuclide generator systems like the $^{62}Zn/^{62}Cu$ generator of U.S. Pat. No. 5,573,747 are compatible with FDA accepted GMP production.

Although the inline synthesis generator as depicted in U.S. Pat. No. 5,573,747 has functioned very well in limited clinical studies, it has deficiencies which prevent it from being commercially viable on the large scale required for clinical use. Considering that any $^{62}Zn/^{62}Cu$ generator can be utilized for only one day, it is essential that every possible step be taken to simplify the system and thereby reduce the cost of production. Also, as to the generator of U.S. Pat. No. 5,573,747, the FDA has expressed a strong concern with regard to the generator septum which is entered repeatedly by the user. Instead, a product "collection directly into an empty sealed, pre-sterilized vial" is preferred and required for maintaining generator sterility. The generator's tubing set of that of U.S. Pat. No. 5,573,747 generator is costly to produce and the FDA also expressed reservations regarding the sterility during reuse. They stated "The product has a complex fluid path. To address this deficiency, you must add measurable tests to document the integrity of the system. However, given the design and recycling, it is doubtful that a test will be sufficient. A design modification may be needed." In addition, inclusion of a pump inside the $^{62}Zn/^{62}Cu$ generator of U.S. Pat. No. 5,573,747 substantially increases the size of the generator housing and contributes to a higher shipping expense. Further, the transport of the large shield required for the 750 µl column is substantial in weight (35 lbs), and the shipping expense makes up a large portion of the cost for the generator system with a 1 day clinical life. Thus all means should be employed to reduce the weight and size of the $^{62}Zn/^{62}Cu$ generator. Another serious limitation is the large 33 mL injectable volume. Such a large volume is required because of the high salt content of the eluant solution, which must be diluted with sterile water for injection (SWFI) to achieve an isotonic solution. This large injection volume requires heavy, bulky shielding to avoid excessive technologist radioactive dose and precludes the convenient vial synthesis technique. Further, the high injection volume can also produce discomfort in some of the more sensitive patients and requires a prolonged injection time, which makes it difficult to define the input function required for typical PET quantitative analysis. Since in the $^{62}Zn/^{62}Cu$ generator of U.S. Pat. No. 5,573,747 the ligand addition is performed within the generator, only a single radiopharmaceutical can be produced without substantial added complexity. This limitation is unfortunate, particularly in light of the availability of the several very useful $^{62}Cu$ radiopharmaceuticals and the attractive applications of closely separated studies using two or more agents. For example, tumor or myocardial perfusion can be immediately followed with a $^{62}Cu$-ATSM hypoxia scan. It can be readily speculated that such a perfusion scan is vital for achievement of a meaningful and quantitative hypoxia score.

There still exists a clear need for a system and method by which easy, interchangeable production of multiple PET radiopharmaceuticals can be accomplished.

A new system accomplishes easy, interchangeable production of multiple PET radiopharmaceuticals through the use of a simplified eluant-only generator and a kit based synthesis technique employing lyophilized or freeze dried ligand. Thus, by simply switching the lyophilized ligand vial kit, any number of $^{62}Cu$-labeled radiopharmaceuticals ($^{62}Cu$-ligand) can be interchangeably synthesized with only one $^{62}Zn/^{62}Cu$ generator. In addition to interchangeable radiopharmaceutical production, use of a lyophilized kit formulation brings substantial benefits of higher stability and lower cost, as is well known in the industry. Further, the unit dose volume of the so produced radiopharmaceutical is greatly reduced, increasing patient comfort and administration time.

BRIEF DESCRIPTION OF THE DRAWINGS

FIG. 6(a) illustrates elution profiles of two generators, one loaded with 1.5 ml of 66.1 mCi $^{62}Zn$ solution (Z122) and the other loaded with 150 µl of 78.0 mCi $^{62}Zn$ solution (Z123), while FIG. 6(b) illustrates the elution profile of one of the generators (Z123) after 48 and 118 bed volumes of eluant passed over the column.

FIG. 14 shows TLC count profiles obtained for $^{62}CuPTSM$ on C18 and silica gel media and for the ionic $^{62}Cu^{2+}$.

Figure 1:
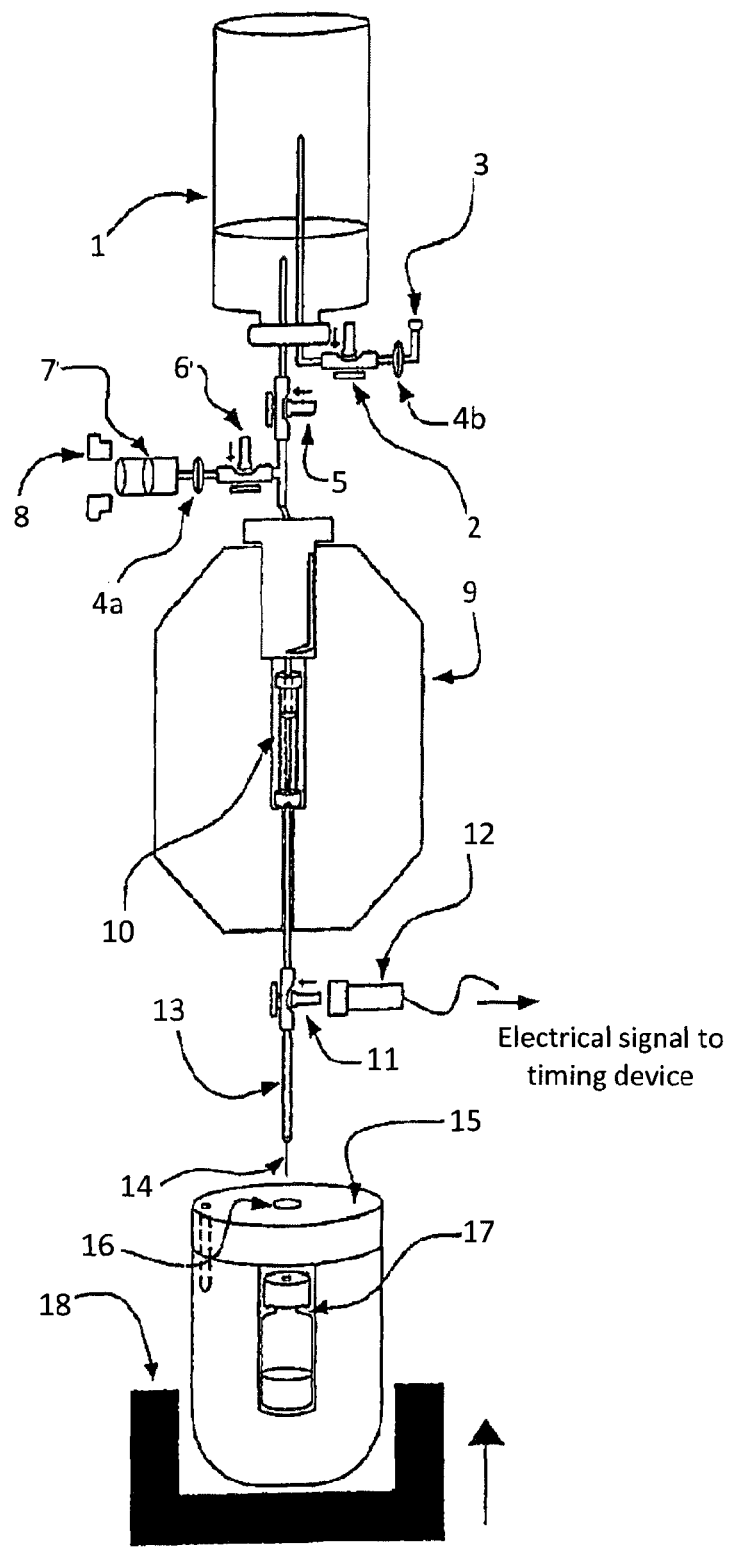
FIG. 1 illustrates a highly simplified and miniaturized generator that produces as an eluant, sterile, pyrogen-free $^{62}Cu^{2+}$ only.

A highly simplified and miniaturized generator is illustrated in FIG. 1 that produces as an eluant sterile, pyrogen-free $^{62}Cu^{2+}$ only. The reduced size of the generator column 10 facilitates the needed reduction in the volume of the eluted $^{62}Cu$. The generator contains only a single eluant reservoir 1 and a small column 10 with a volume of 25-100 µL that is eluted by a modest pressurization in the sealed eluant reservoir 1. In a preferred embodiment, the column contains a beaded or particulate medium having a small volume of 25-100 µl. The pressurization streamlines and simplifies the loading and elution process and removes the peristaltic pump as the $^{62}Zn/^{62}Cu$ generator of U.S. Pat. No. 5,573,747 requires. The miniaturization of the column is possible because the mass of 50 mCi of $^{62}Zn$ is only 10 ng, which represents 0.8% of the binding capacity of just 1 µL of AG1X8 resin beads. This innovation accomplishes a 15 fold reduction in column volume, and together with use of modern tungsten shielding alloys 9 and the removal of the peristaltic pump, drastically reduces the weight of shielding needed around the column, leading to a sizable decrease in shipping expense. However, the most significant benefit of the column size reduction is that the injectable volume of the radiopharmaceutical product is reduced by a commensurate factor of 15. Since the salty 1.8 M NaCl, 0.2 M HCl eluant solution, together with a NaAc buffer, must be diluted six-fold to reach isotonicity, small elution volumes are essential for a lyophilized ligand kit synthesis approach. By effecting this large reduction in elution volume, the miniaturized generator or "microgenerator" permits production of an isotonic injectable PET radiopharmaceuticals in a receiving vial 17 of practical size (i.e. <5 mL).

The $^{62}Zn/^{62}Cu$ microgenerator is illustrated in FIG. 1 and contains four main parts: a resin microcolumn 10, an eluant vessel 1, a loading port 8 and an elution port 14. The key component of the system is the greatly size reduced borosilicate glass column. In one embodiment this column is 2.9 cm in total length, with an interior diameter of 2 mm and an outer diameter of 6 mm. The top and bottom of this column are formed into standard 8 mm vial closures. A 3 mm thick, 30 micron pore size glass frit is fused 5 mm from the bottom of the column. The column is filled to a calibration line with a 50 µl volume of AG1X8, 200-400 mesh anion exchange resin. Entry and exit from the column are provided by short pieces of 19.5 gauge (1 mm OD, 0.7 mm ID) corrosion resistant metal tubing (i.e., Inconel 625). To minimize void volume in the column, the tubing at the entry and exit of the column protrude through the 1.6 mm×7 mm Viton septum. A 0.5 mm hole in the septum facilitates the entry of the tubing which is introduced following crimp sealing with 8 mm aluminum crimp seals. The precise dimensions of the microcolumn 10 are not critical beyond the fact that the column is dimensioned to provide a single unit dosage of $^{62}Cu$ eluant which when mixed with SWFI yields an isotonic injectable solution of not greater than about 5 mL volume.

Figure 2:
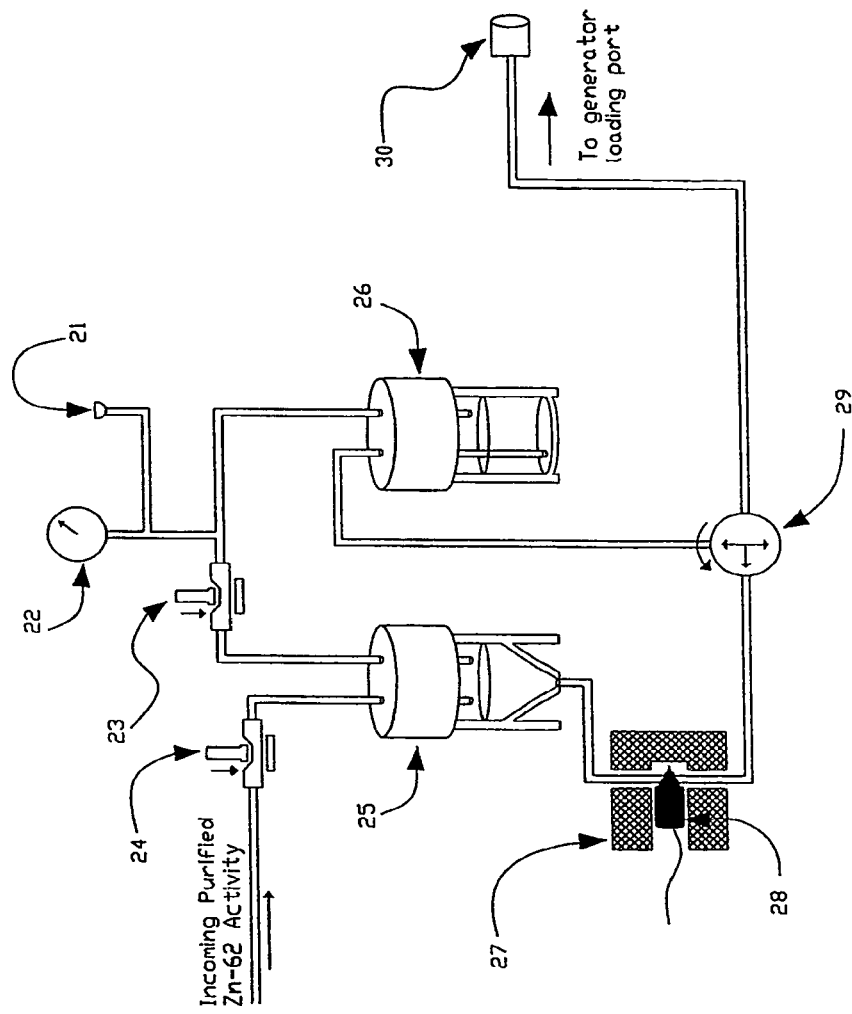
FIG. 2 illustrates a loading apparatus which is used to load the generator of FIG. 1 with $^{62}Zn$.

A "T" fitting above the column allows input connections from the eluant vessel 1 or the loading port 8 to the column 10 through the manipulation of pinch valves 5 and 6 operating on short sections of flexible tubing (i.e., Pharmed tubing [Cole-Parmer]). To assure sterility after autoclaving and to prevent contamination due to non-sterile fluids entering the system, a 0.22 µm hydrophilic (PVDF) sterilizing filter 4a is placed in the load line. At the end of the load line, an HPLC fitting 7 allows simple, sterile connection and disconnection of the generator to the loading apparatus which is illustrated in FIG. 2. A pinch valve 11 of FIG. 1, controlled by a solenoid or manual actuator 12 is located below column 10. Opening and closing pinch valve 11 controls the elution process. Placement of the valve below the column 10 maintains constant pressure within the resin bed of the column and thereby prevents gas bubble formation produced by dissolved gases. Below this pinch valve is a rigid needle support 13 which assures the rigidity of needle 14 during its insertion through a septum of a kit vial 17. As FIG. 1 illustrates, a vial shield 15 is provided which has a removable top which has an entry port 16 positioned above the vial cavity within vial shield 15. The entry port provides access to the septum of vial 17 by the elution needle 14 of the generator as a lifting and alignment mechanism 18 moves a lyophilized ligand vial 17 within vial shield 15 into registration with elution needle 14.

The eluant vessel may be a 50 ml serum vial with a 20 mm grey butyl septum and aluminum crimp seal. The flow rate through the column is controlled by pressure maintained in the head space of this vessel. The bottle is pressurized by a pressure source 3 through a 0.22 µm hydrophobic (PTFE) sterilizing filter 4b and sealed with a pinch valve 2 as shown in FIG. 1.

The loading apparatus is illustrated in FIG. 2 and is also set up for an air-pressure driven delivery system. A 3 ml conical Teflon vial 25 is used as the loading vessel. To modify this vessel for use as a loading vessel, a slightly undersized hole is drilled in the bottom and the vessel is heated to 100° C. After heating a 0.5 mm ID length of 1.6 mm OD tubing (i.e., Teflon) is quickly inserted into the opening. Upon cooling, the line is securely retained through thermal compression. This line passes over a shielded Geiger probe 28 (which is shielded 27) placed 2 cm below the loading vessel 25, which provided a rapidly responding indication of the presence or absence of radioactive solution in the tubing.

Two punctures are made in the loading vessel lid septum to allow the entrance of 0.5 mm ID tubing (i.e., Teflon). One is used to pressurize the loading vessel and the other is employed to transfer purified $^{62}Zn$ into the loading vessel. A pinch clamp 23 located on the air pressure line leading to the loading vessel 25 allows a pressure difference between the washing vessel 26 and the loading vessel 25 for filling of the interconnecting liquid flow path. Pressure applied from a pressure source 21 is accurately measured using a digital pressure transducer 22 (i.e., Omega PX170). Connections between the pressure source to the washing and loading vessels are made using 0.5 mm ID Teflon tubing. Tygon tubing (1.5 mm ID) connects the pressure transducer to the loading pressure system.

The washing vessel 26, like the loading vessel 25, has two punctures in the septum for the insertion of 0.5 mm ID tubing. One line pressurizes the washing vessel and the other line supplies 2M HCl to the loading line. The lines that flow from the loading vessel and the washing vessel terminate in a 3-way HPLC selector valve 29. This valve allows flow from the washing vessel to the loading vessel, for liquid line filling, from the loading vessel to the loading port 8 of the generator (FIG. 1), for generator loading, and from the washing vessel to the loading port 8 of the generator for liquid line filling and generator loading. At the end of the load line on the loading apparatus, an HPLC quick connect 30 is provided for connection to the generator load port 8.

A load activity (i.e., $^{62}Zn$), is pumped into the conical loading vessel 25 of FIG. 2, following preparation of the loading system, which includes filling of all lines with 2M HCl from the washing vessel. The loading procedure is as follows. The pinch clamp 23 is closed under atmospheric pressure to facilitate filling of the line originating at the 3-way HPLC valve 29 and ending at the loading vessel 25 with 2M HCl from the washing vessel 26. The 3-way valve is then turned to select the flow path from the washing vessel to the load line to liquid fill that line as well. The output 30 of the load apparatus is connected to the loading port 8 of the generator in a manner assuring liquid continuity with no air bubbles. The pinch clamp 5 leading from the eluant vessel 1 to the "T" fitting is closed to prevent flow of $^{62}Zn$ into the eluant vessel, and 2M HCl is then delivered from the washing vessel 26 (FIG. 2) through the generator column 10 to verify that the desired loading flow rate is achieved. The 3-way valve is switched to direct $^{62}Zn$ solution from the loading vessel 25 to column 10 of the generator. During the loading procedure, an eventual rapid drop in Geiger probe 28 reading signals a switch of the 3 way valve from the loading vessel to the washing vessel. The column 10 of the generator is then washed with 256 µl of eluant, after which the loading vessel is detached and the column 10 of the generator is ready for use.

Figure 8:
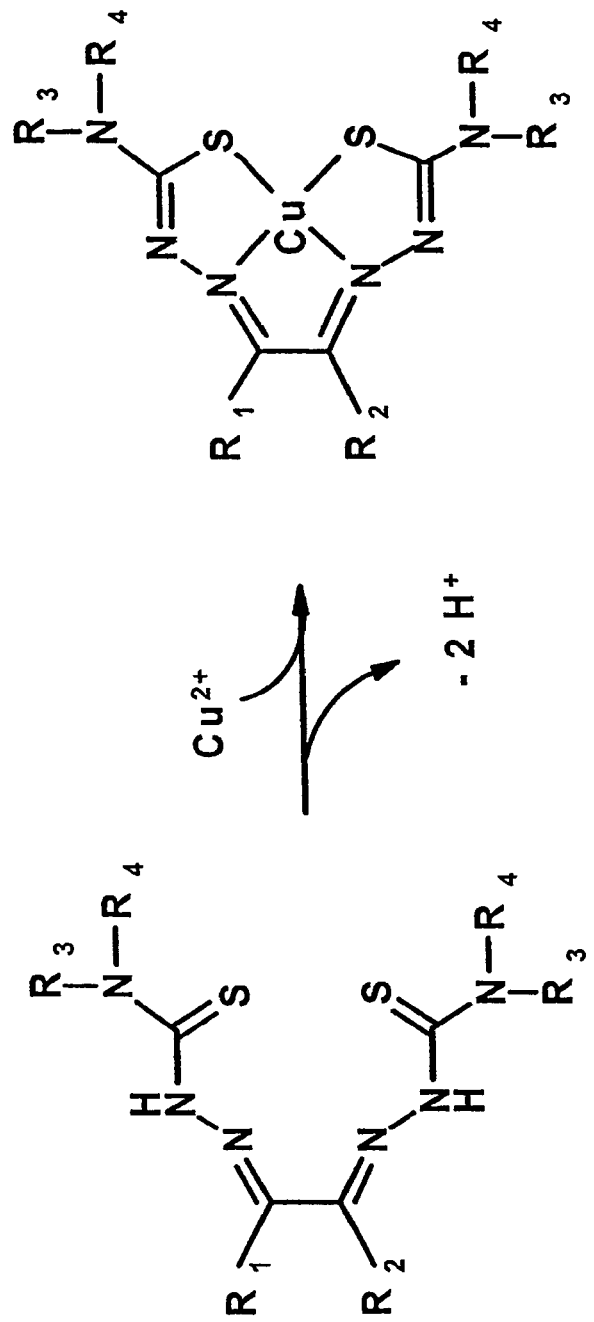
FIG. 8 depicts the chelation of a copper (II) ion, which is effective regardless of the substitution of side groups, $R_x$ (where x=1, 2, 3, or 4).

All of the bis(thiosemicarbazone) derivatives readily and avidly chelate Cu in the same manner. FIG. 8 depicts the chelation of a copper (II) ion, which is effective regardless of the substitution of side groups, $R_x$ (where x=1, 2, 3, or 4). This is because the $Cu^{+2}$ ion interacts with the hybrid orbitals of nitrogen and sulfur atoms in the compound in a manner little influenced by the composition of $R_x$. The conjugated π-system within the ligand is conserved in this reaction and the substituted groups, which are outside of this conjugated system, do not participate in the mechanism of chelation. When the copper ion binds to the sulfur atoms, there is a rearrangement of electrons, which results in the formation of two nitrogen-carbon double bonds and the loss of two H+ atoms. In the complexed ligand, the copper atom is bound in a square configuration which is common for copper in its 2+ state. Table 1 is a partial list of bis(thiosemicarbazone) complexes which have been reported in the literature.

The structure of the bis(thiosemicarbazone) complexes is as follows:

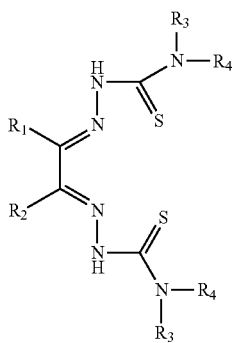

TABLE 1

Partial list of Copper bis(thiosemicarbazone) complexes

| | $R_1$ | $R_2$ | $R_3$ | $R_4$ |
|---|---|---|---|---|
| GTS | H | H | H | H |
| GTSM | H | H | $CH_3$ | H |
| PTS | $CH_3$ | H | H | H |
| PTSM | $CH_3$ | H | $CH_3$ | H |
| $PTSM_2$ | $CH_3$ | H | $CH_3$ | $CH_3$ |
| ETS | $CH_2CH_3$ | H | H | H |
| ETSM | $CH_2CH_3$ | H | $CH_3$ | H |
| $ETSM_2$ | $CH_2CH_3$ | H | $CH_3$ | $CH_3$ |
| PTSE | $CH_3$ | H | $CH_2CH_3$ | H |
| PTSP | $CH_3$ | H | $C_6H_5$ | H |
| ATS | $CH_3$ | $CH_3$ | H | H |
| ATSM | $CH_3$ | $CH_3$ | $CH_3$ | H |
| CTS | $CH_2CH_3$ | $CH_3$ | H | H |
| CTSM | $CH_2CH_3$ | $CH_3$ | $CH_3$ | H |
| DTS | $CH_2CH_3$ | $CH_2CH_3$ | H | H |
| DTSM | $CH_2CH_3$ | $CH_2CH_3$ | $CH_3$ | H |

TABLE 2

Partition coefficients of selected Cu bis(thiosemicarbazone) complexes

| | $R_1$ | $R_2$ | $R_3$ | $R_4$ | log P* |
|---|---|---|---|---|---|
| ATSM | $CH_3$ | $CH_3$ | $CH_3$ | H | 2.26 |
| PTSM | $CH_3$ | H | $CH_3$ | H | 1.92 |
| ETS | $CH_2CH_3$ | H | H | H | 1.35 |

From measured octanol/water partition coefficients, P, of the corresponding $^{67}$Cu-complexes.

Although the chelation chemistry of these compounds is very similar, they exhibit very different chemical and physical properties in vivo due to their differing side Rx groups. For example, $H_2ATSM$ and $H_2PTSM$ differ by only the $R_2$ side-group but have octanol/water partition coefficients that differ by 0.34 (Table 2). Different side group substitutions can also substantially alter the binding of the copper compound to various components of the blood. Such effects have been shown to be highly species dependent. In particular, Cu-PTSM exhibits low binding to blood in most animal species other than humans, but exhibits significant binding in humans, which causes non-linear uptake at high flow levels. The variant Cu-ETS, on the other hand, has low reversible binding to blood plasma and thus proves to be a more effective perfusion tracer than Cu-PTSM in applications in which high blood flow organs such as heart and kidney are imaged.

Figure 9:
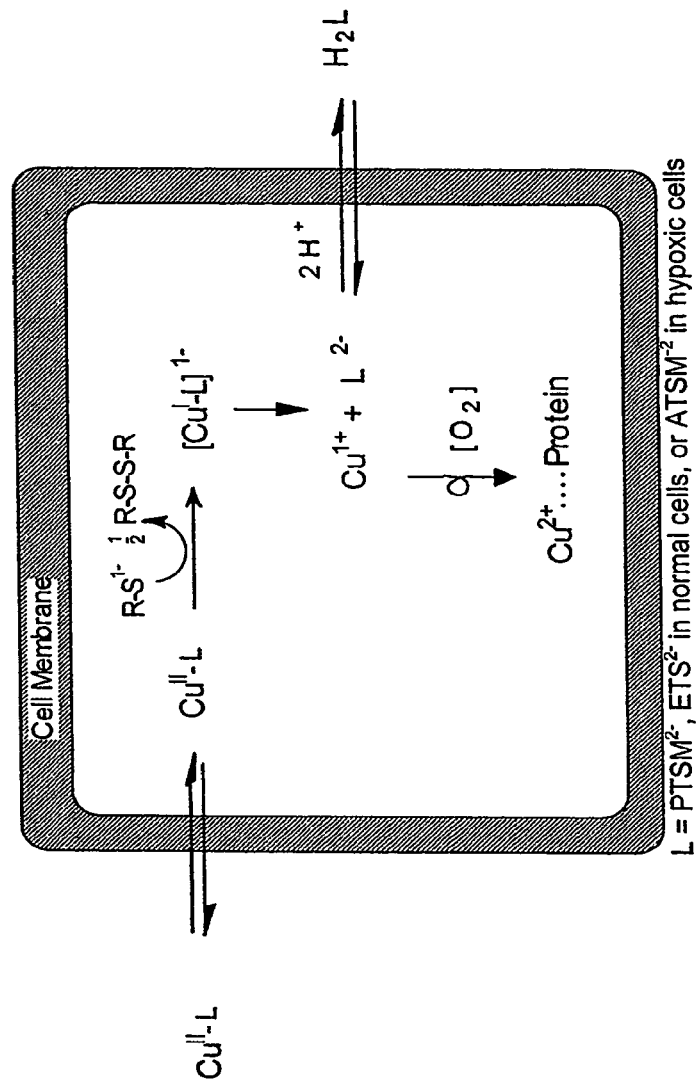
FIG. 9 illustrates the thiol-mediated intracellular decomposition of CuII-PTSM that is believed to account for the prolonged "microsphere-like" tissue retention of the $^{62}Cu$-radiolabel following intravenous administration of this and related $^{62}Cu$-bis(thiosemicarbazone) complexes in normal cells.

FIG. 9 illustrates the thiol-mediated intracellular decomposition of CuII-PTSM that is believed to account for the prolonged "microsphere-like" tissue retention of the $^{62}$Cu-radiolabel following intravenous administration of this and related $^{62}$Cu-bis(thiosemicarbazone) complexes in normal cells. The uncharged lipophilic copper(II) bis(thiosemicarbazone) complexes readily diffuse across cell membranes, whereupon they are susceptible to reductive decomposition by reaction with ubiquitous intracellular thiols, such as glutathione. Electron transfer from the thiol sulfur to the CuII-bis(thiosemicarbazone) complex leads to dissociation of CuI from the bis(thiosemicarbazone) ligand to become bound (and effectively trapped) by intracellular macromolecules. Different CuII-bis(thiosemicarbazone) complexes have distinct reduction potentials, which significantly effects intracellular trapping. CuATSM, for example, has a lower redox potential than CuPTSM or CuETS at 100 mV. As a result it is not reduced in normoxic tissues and therefore quickly washes out. However, in hypoxic tissues, the Cu(II) of CuATSM is quickly and irreversibly reduced to Cu(I) and retained due to the lack of electron carrier (Oxygen).

The new method for synthesizing radiolabeled Cu-bis(thiosemicarbazone) compounds centers on the utilization of a lyophilized form of the ligand. Lyophilization or freeze drying is a process in which water is removed from a product after it is frozen and placed under a vacuum, allowing the ice to sublime directly from solid to vapor without passing through a liquid phase. This process can effectively prevent the crystallization of the solute thereby rendering it far more readily soluble than normally would be the case in solid form. After sterile lyophilization, the dry resulting cake remains sterile and can be stored for a much longer period of time than if it had remained in an aqueous solution as is very well known in the pharmaceutical industry. Solutions containing the ligand of interest are lyophilized with an excipient and stored in 2-5 ml vials. The vial contents can be virtually instantaneously rendered soluble (reconstituted) by simple addition of sterile water for injection (SWFI) or with SWFI containing a buffer agent such as Sodium Acetate. Sterile radioactive $Cu^{+2}$ solution from the $^{62}Zn/^{62}Cu$ generator or other source can then be added to the vial for instantaneous formation of the radiolabeled Cu-ligand complex. Such instant synthesis is essential for practical clinical use of such a short-lived agent as $^{62}Cu$ ($t_{1/2}$=9.7 min). In the case that $^{62}Cu$ is obtained from the $^{62}Zn/^{62}Cu$ generator the solution optimally consists of 1.8M NaCl, 0.2M HCl and the vial contents most optimally contain a 2 molar excess of sodium acetate or other buffer and a volume of SWFI which together with the $^{62}Cu$ bearing solution brings the osmotic pressure of the final injectable solution to a value near that of blood (7.7 atm) and produces a pH most optimally in the range 5.5-7.0.

Studies evaluating the compatibility of the bis(thiosemicarbazone) ligands with lyophilization based kit synthesis were conducted using $H_2PTSM$ as a model compound. The first of these studies evaluated the feasibility of ligand lyophilization and rapid reconstitution. The entire class of bis(thiosemicarbazone) compounds is very insoluble in water.

Consequently, in order to prepare a principally aqueous solution for lyophilization, the crystalline form of the H$_2$PTSM was dissolved at the maximum concentration in dimethylsulfoxide (DMSO), (200 mg/mL H$_2$PTSM). Because of high ligand solubility in DMSO, very small volumes of this solution added to water produced a nearly DMSO-free aqueous solution of the ligand having a concentration of 2 μg/mL. To minimize the possibility of ligand precipitation, the DMSO solution was added to hot water (90° C.) during rapid stifling. This solution was then cooled to room temperature and assayed for potency using a spectrophotometer. The very small amount of DMSO in the aqueous solution is expected to sublimate along with water during lyophilization. In order to ensure maximum potency after lyophilization, an excipient (either dextrose [6.7 mg/mL], trehalose [6.7 mg/mL] or sodium acetate [5.4 mg/mL]) was added. The purpose of the excipient was to prevent the ligand from crystallizing out by maintaining dispersion in the cake formed during lyophilization. The sodium acetate performed the added function of buffering the final product to acceptable pH upon addition of 0.1-0.15 mL of $^{62}$Zn/$^{62}$Cu generator eluted solution. Any true crystallization of the ligand must be avoided because such crystallized forms are extremely difficult to bring back into aqueous solution. The solution consisting of 2 μg/mL ligand together with excipient was aliquotted 1 ml per 2-mL vial and sent for lyophilization. The lyophilization of the vials was performed by first freezing the samples to −70° C. for a 2-hour period then equilibrating the vials (in the lyophilizer) at −20° C. for two hours. Finally, refrigeration was terminated and an 18-hour vacuum (25-50 mtorr) cycle was started. At the end of the vacuum cycle the vials were crimp-sealed under nitrogen gas.

EXAMPLES

Example 1

To evaluate the pressure method of delivery of eluant through the generator column, the pressure in the elution vessel was varied and the flow rate was determined by measuring the eluted volume per unit time. The desired elution flow rate is estimated by scaling from the 750 μL column generator, which elutes at 3.6 ml/min. By scaling this flow rate in accordance with the ratio of resin bed volumes in each design, a 240 μl/min flow rate for the new system was predicted. The eluant vessel initially contains 5 ml of eluant. With a maximum estimated clinical column usage of 20 elutions with approximately 0.12 ml per elution volume, there is a 2.4 ml reduction in eluant volume, producing only a 5% change in elution pressure and therefore a negligible variation of flow rate over a day of clinical use, which is the maximum shelf life in routine clinical use.

The method of pressure driven elution achieved the targeted elution rate of 240 μl/min. The eluant vessel was empirically pressurized over a range of pressures between 5-15 psig. The eluted samples were then weighed to determine the flow rate under a specific pressure. In order to investigate the effect of variable flow rate on column performance, elution profiles at various pressures were collected in fractions of 5 or 10 seconds over 30, 60, or 120 second periods. All elutions and fractions were immediately measured in a Capintec CRC-15R and decay corrected to the beginning of elution. These elutions and fractions were also weighed to determine the volume eluted per unit time.

Preliminary pilot studies of the simplified microgenerator and vial synthesis approach were performed. A primary purpose of these studies was to demonstrate the production feasibility and acceptable performance of a generator column of greatly reduced physical size and volume. Secondarily, the feasibility of simple methods of column elution with passive pressure, rather than a pump, were explored.

A total of four columns were loaded and evaluated. All four columns were loaded at a flow rate of 10 μl/min. Variable load volumes were assessed to evaluate the effect on breakthrough and yield performance. Volumes ranged from 0.15 ml to 1.5 ml. Load activity was sequentially increased to assess any potential radiation damage effects on the performance of the column. Activity ranged from 2.9 mCi to 78 mCi.

Breakthrough of selected eluted samples was counted following full decay of $^{62}$Cu in a NaI well counter (Searle model 1197) (4 hours post elution). Purified $^{62}$Zn was used to calibrate the system. Breakthrough is reported as the ratio of $^{62}$Zn in the eluant solution divided by the $^{62}$Zn on the generator column, both decayed to the same point in time.

Four prototype microgenerators were constructed. Each employed a 50-mL glass eluant vessel directly connected by tubing to a 50-μL resin-filled column, which was coupled to an output tubing line. Elution was controlled by opening and closing a calibrated manual pinch clamp. The clamp was designed and adjusted to avoid exerting excess pressure on the tubing. To pressurize the eluant reservoir, a pressure source was connected to the tubing line leading to the head space of the vessel (see FIG. 1; 3). In order to demonstrate the feasibility of pressure-driven flow and to establish the relation between pressure and flow rate, elution samples were collected and weighed for vessel pressures ranging from 0-15 psig. In addition, careful studies were performed to establish the flow rate reproducibility. A solution of $^{62}$Zn was loaded onto each column at a load rate of 10 μL/min. To assess the potential radiation effects on the very small resin bed, activities ranging from 2.9 mCi to 78 mCi were explored. The effect of load volume, which ranged from 0.15 mL to 1.5 mL, on $^{62}$Cu yield and $^{62}$Zn breakthrough was also investigated. For each generator, elution samples of 30 and 60 second duration were collected frequently over a period of two days. Serial elution samples were also collected in 5- or 10-second fractions. Sample activity levels were assayed in a dose calibrator (Capintec CRC-15) and decay corrected to obtain elution profiles and yield estimates. Following decay of $^{62}$Cu (>4 hrs post elution), samples were counted in a NaI to measure breakthrough.

Figure 3:
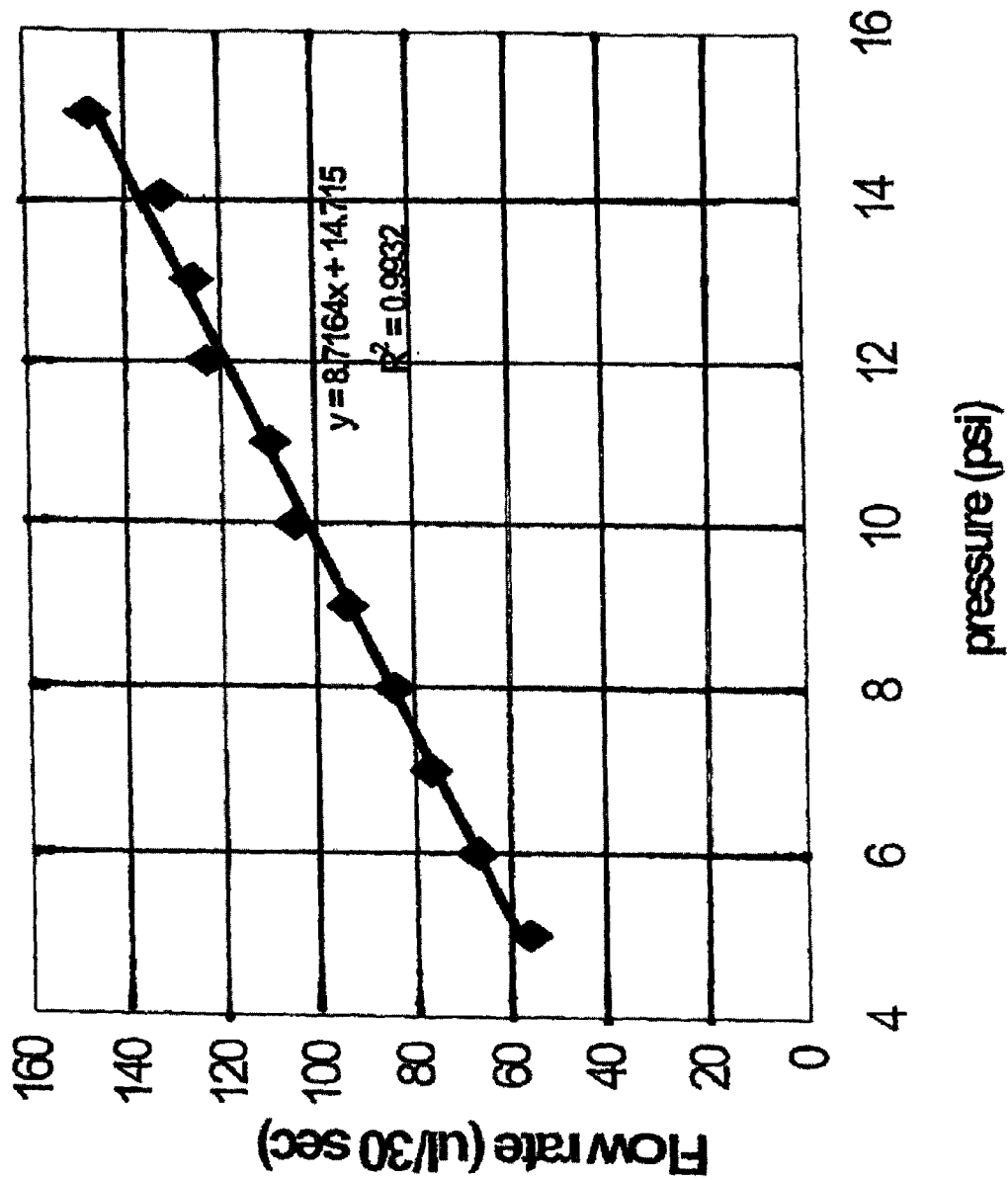
FIG. 3 illustrates the relation between flow rate of eluant from the generator of FIG. 1 and pressure introduced into the head space of the eluant vessel of the generator of FIG. 1.
Figure 4:
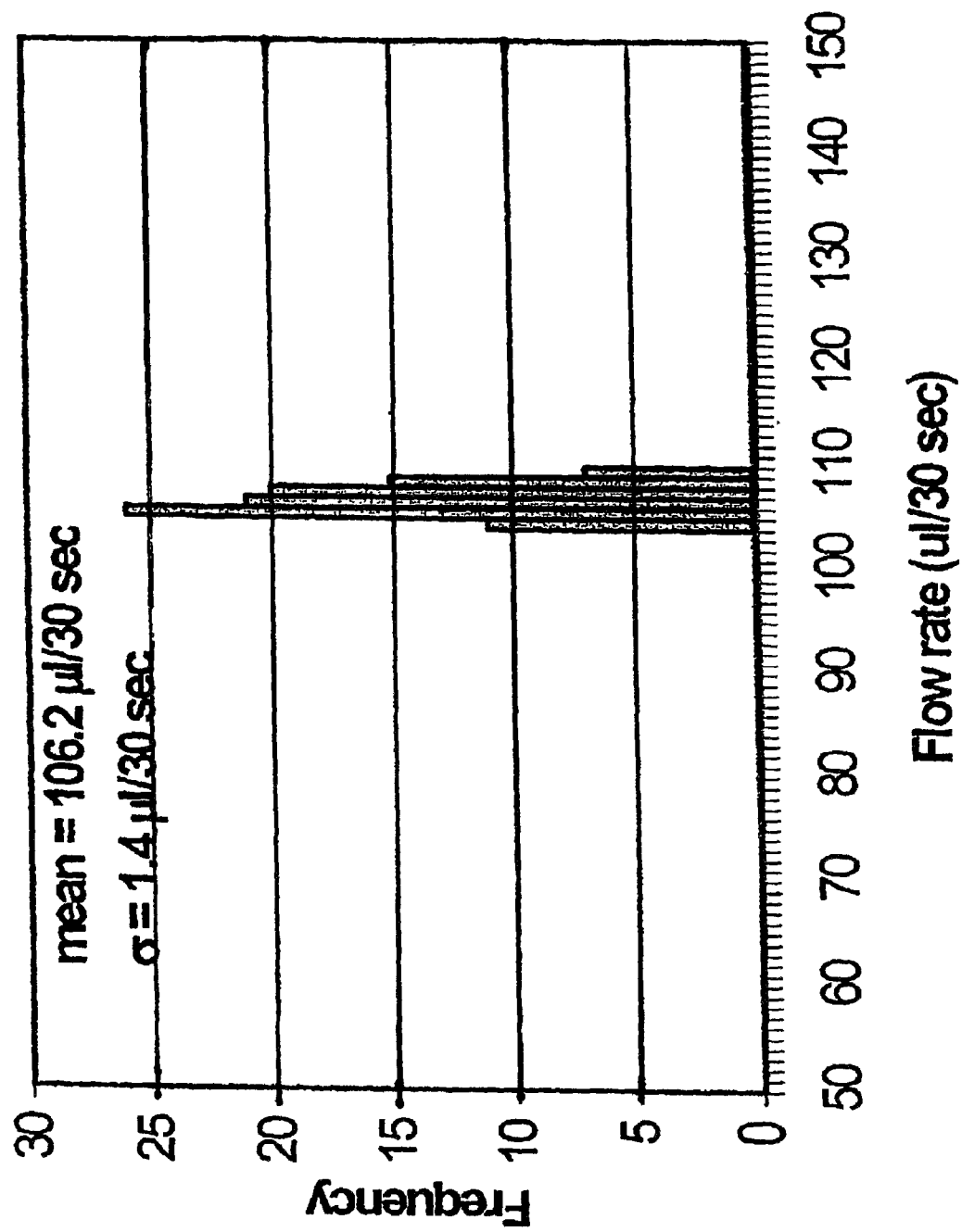
FIG. 4 illustrates the reproducibility of flow rate of the generator of FIG. 1.

In flow rate studies, results indicated that pressures of 1-2 psig were adequate to achieve the desired flow rates of 50-200 μL/30 sec. At such low pressures, however, changes in temperature and eluant volume produced significant changes in flow rate. In order to attenuate the impact of these factors, vessel pressure was increased roughly ten-fold, and studies of the pressure-flow rate relation were repeated for pressures of 5-15 psig. Corresponding increases in the length of the small I.D. tubing between the eluant vessel and the column were incorporated to maintain the desired flow rates at these higher pressures. As shown in FIG. 3, flow rate and vessel pressure displayed a very tight linear relation. Thus, the optimal flow rate, once established, clearly can be achieved through choice of the corresponding vessel pressure. Studies also demonstrated that pressure-driven flow is highly reproducible, as illustrated by the narrow peak in FIG. 4. At 10 psig, a 30-second elution dispensed a mean volume of 106.2 μL with a standard deviation of <1%.

The equation shown in FIG. 3 and the ideal gas law may be used to estimate the effect of changes in eluant volume and temperature on the volume delivered in a 30 second elution. Assuming an initial vessel pressure of 10 psig, which produces a flow rate of ~106 μL/30 sec, and an initial temperature of 77° F., a decrease in temperature of 10° F. would lower delivered volume by only 4.0 μL. A decrease in eluant volume of 2.12 mL, which corresponds to twenty 106 μL elutions, would lower delivered volume of roughly 9.7 μL. Such changes in eluant volume and ambient temperature represent fairly extreme conditions of clinical use. Even in the unlikely event that they occur together, they would produce only modest changes (<13%) in delivered volume, which is reasonable in the context of clinical applications.

Figure 5:
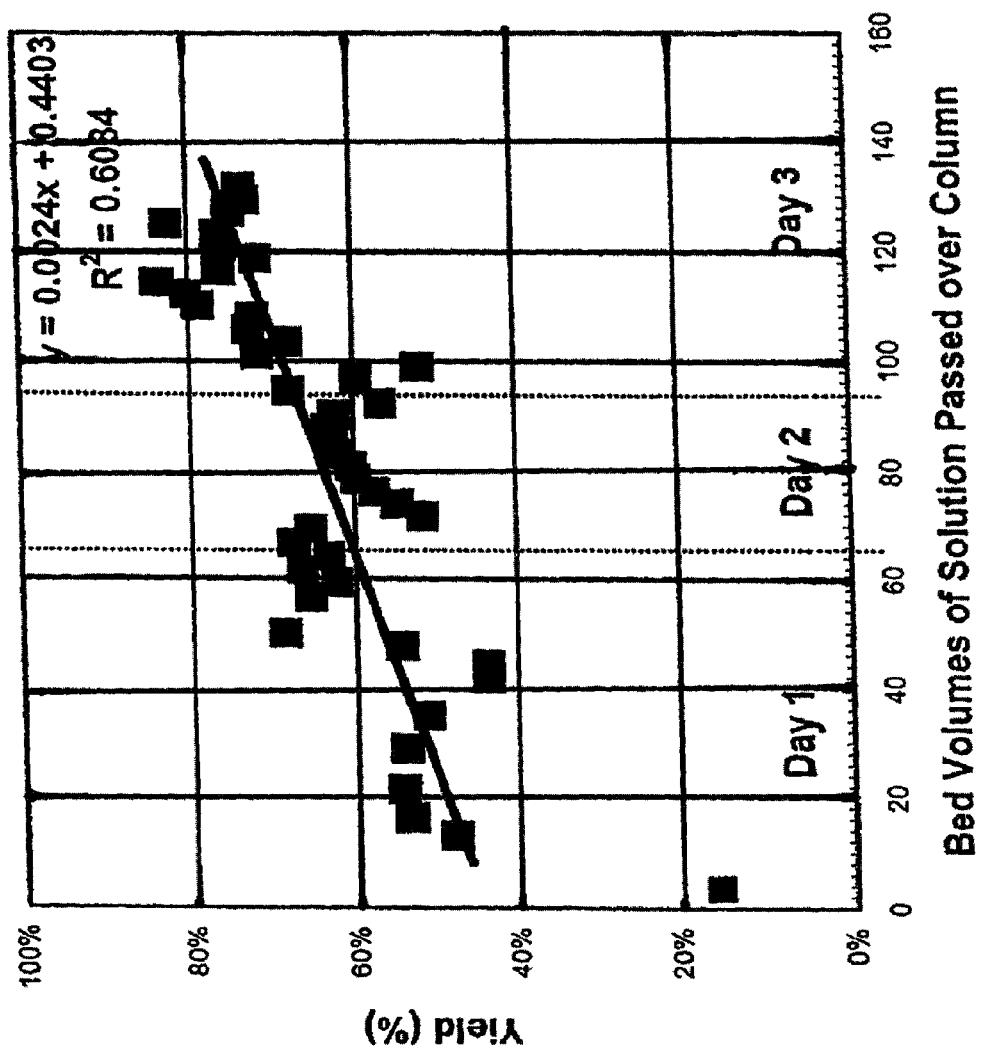
FIG. 5 illustrates the yield ($^{62}Cu$ eluted/$^{62}Zn$ on column) vs. bed volumes of eluant passed over the column of the generator of FIG. 1 (Z122).

Prototype microgenerators performed very well in pilot studies. Table 3 lists the yield and breakthrough data for the four microgenerators and a typical current clinical generator. For all of the prototype generators, the average yield values ($^{62}$Cu eluted/$^{62}$Zn on column) for the first 30 seconds of elution were equivalent to or greater than current generator yields of roughly 50%. These results clearly support the hypothesis that adequate yield can be obtained using a miniaturized column. Furthermore, as shown in FIG. 5, high yields were maintained under conditions of frequent elution throughout the two day testing period.

Figure 6:
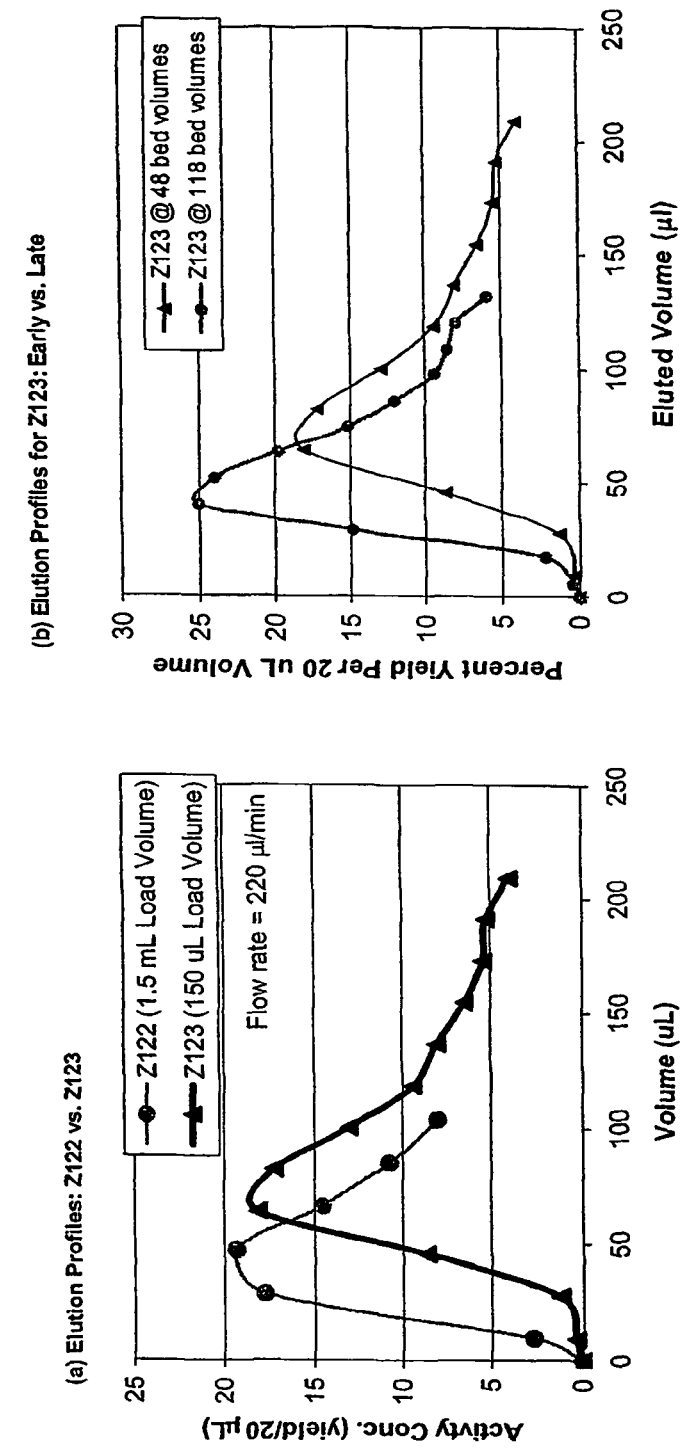

Pilot studies revealed multiple factors that affect generator performance. Firstly, over time, as more eluant was washed over the resin column, yield increased (see FIG. 5). Secondly, reduced load volume may initially produce lower yield. For example, generator Z123 was loaded with a ten-fold smaller volume than Z122 (150 μl vs. 1.5 ml) and also produced a roughly 10% lower average yield (see Table 1). Presumably, under conditions of lower load volume, the $^{62}$Zn activity binds to the resin in a narrow band close to the top of the column. As a result, a greater volume must flow over the resin before the $^{62}$Cu reaches the column output. Elution profiles (see FIG. 6) support this hypothesis. In these profiles, activity concentration is plotted against eluted volume. As shown in FIG. 6(*a*), Z123 shows a much later activity peak than Z122. As a result, for generators with low load volume, more of the peak and tail are cut off, in a 30-second elution, resulting in a lower yield. As suggested by FIG. 5, this yield may rise after adequate eluant has passed over the resin bed. FIG. 6(*b*) displays elution profiles for Z123 taken after 48 and 118 bed volumes of eluant had been passed over the column. As shown, the later profile shows an earlier and narrower peak.

TABLE 3

Summary performance data for pilot microgenerators

| Gen. ID | Load Activity (mCi) | Load Volume (ml) | Average 30 s % yield | $^{62}$Zn breakthrough fraction (Initial levels) |
|---|---|---|---|---|
| Typical current generator | 150 | ~9 | 49-55% | $2.60 \times 10^{-7}$ |
| Z120 | 2.9 | 0.95 | 63% | N/A |
| Z121 | 18.4 | 1.0 | 76% | $3.54 \times 10^{-7}$ |
| Z122 | 66.1 | 1.5 | 65% | $2.56 \times 10^{-7}$ |
| Z123 | 78.0 | 0.15 | 54% | $3.77 \times 10^{-8}$ |

Figure 7:
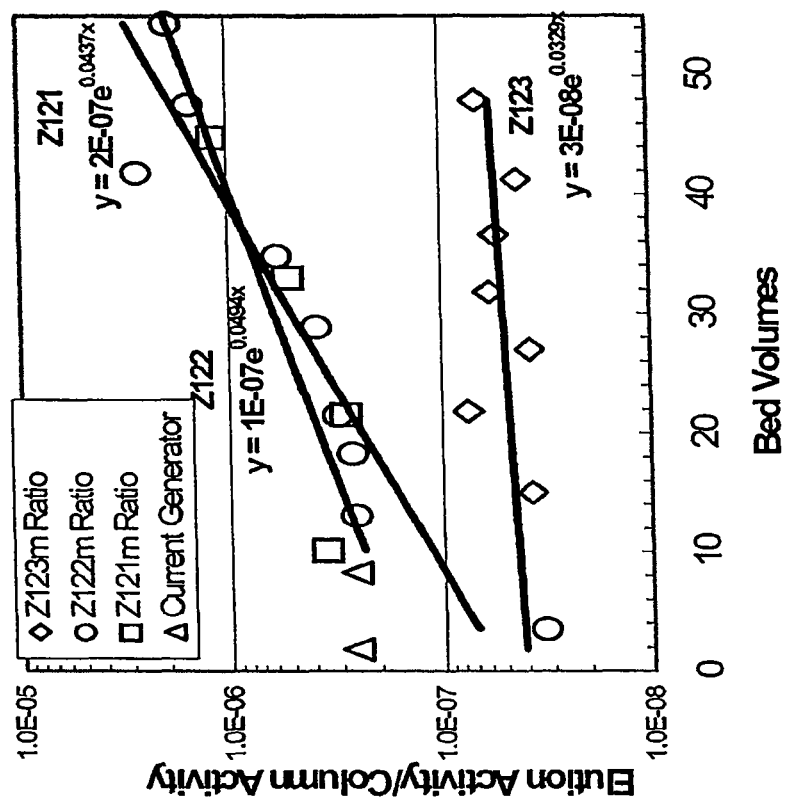
FIG. 7 illustrates the breakthrough levels of $^{62}Zn$ several generators at different loading of $^{62}Zn$.

The results in Table 3 also show that breakthrough of the $^{62}$Zn parent isotope can be maintained well below levels achieved with the modular generator of U.S. Pat. No. 5,573, 747. Microgenerators that were manufactured with larger load solution volumes (i.e. Z121-122) showed breakthrough that was comparable to that of current clinical generators. However, generator Z123, which was loaded using a smaller volume of more concentrated $^{62}$Zn solution, produced an order of magnitude reduction in initial breakthrough levels. Lower load volume also proved advantageous for maintaining low breakthrough levels (see FIG. 7). Z123, which was loaded with the lowest volume, showed, at most, a 2-fold increase in breakthrough after passage of ~40 bed volumes of eluant (~20 elutions) compared to an increase of approximately 10-fold for Z121 and Z122.

In summary, the results of pilot studies showed that a dramatically miniaturized column can perform as well as current generators with respect to important parameters, such as yield and breakthrough, and that such performance can be maintained over the course of expected clinical use. They also suggest a scaled down column may even enable superior performance. Pilot study results also showed that pressure-driven elution was highly reproducible and that variability in delivered volume would be within acceptable limits. Taken together, these findings strongly support the feasibility of the proposed microgenerator design.

Example 2

Tests were run on randomly selected lyophilized vials to compare the concentration of the ligands before lyophilization and after reconstitution. A reliable and sensitive technique for measurement of bis(thiosemicarbazone) ligand concentration was made using UV/VIS spectroscopy. This technique is based upon the ligand's avid chelation of ionic copper and the distinct visible absorbance peak of the resulting copper compound. The contents of each vial were reconstituted with 1.0 mL of deionized water and were diluted to 3.0 mL in a quartz spectrophotometer cuvette, resulting in a concentration of 0.67 μg/mL based on 100% recovery into solution. An excess of $CuCl_2$ (1 μg) was added to permit quantitative formation of Cu-PTSM. This process was performed quickly (2-3 min), and the UV/VIS spectra was measured within 30 seconds. In this manner, the feasibility of rapid reconstitution was assessed. Spectra were obtained for the Cu-PTSM in the three excipient solutions (dextrose, trehalose, or sodium acetate) and for a Cu-PTSM reference solution without excipient.

A second study evaluated the feasibility of in-vitro radiolabeling of reconstituted lyophilized ligand with microgenerator-produced $^{62}Cu^{2+}$ to produce $^{62}$CuPTSM with high radiochemical purity. Formation and purity of Cu-PTSM was assessed using thin layer chromatography (TLC). Lyophilized $H_2$PTSM (2 μg) and trehalose excipient were reconstituted in the lyophilization vial with 105 μL of 0.4 M sodium acetate (i.e. buffer) and 1.5 mL of DI water, thus providing a 2-fold molar excess of buffer and water dilution necessary to reach isotonicity upon addition of 105 μl of generator eluant (1.8 M NaCl, 0.2 M HCl). The vial was vortexed for 30 seconds and then was left to sit undisturbed for 10 minutes. The vial's rubber stopper was removed, and the microcolumn was eluted to deliver 105 μL directly into the vial. The solution mixture was then gently swirled for a few seconds and left to sit at room temperature for 30 seconds. Immediately thereafter, duplicate 0.5 μL aliquots were spotted at the 1.0 cm mark on C18 and silica gel TLC plates. The glass plates were immediately placed in the development tank and were developed for 30 minutes in 100% ethanol mobile phase. In addition, reference ionic $^{62}Cu^{2+}$ plates were run separately. In this test, any ionic $^{62}$Cu remains at the origin whereas the lipophilic $^{62}$CuPTSM compound travels with the solvent. A straw detector-based scanner was used to count the activity distribution on each track of each plate. A minimum of 10,000 counts was acquired for each track.

Figure 10:
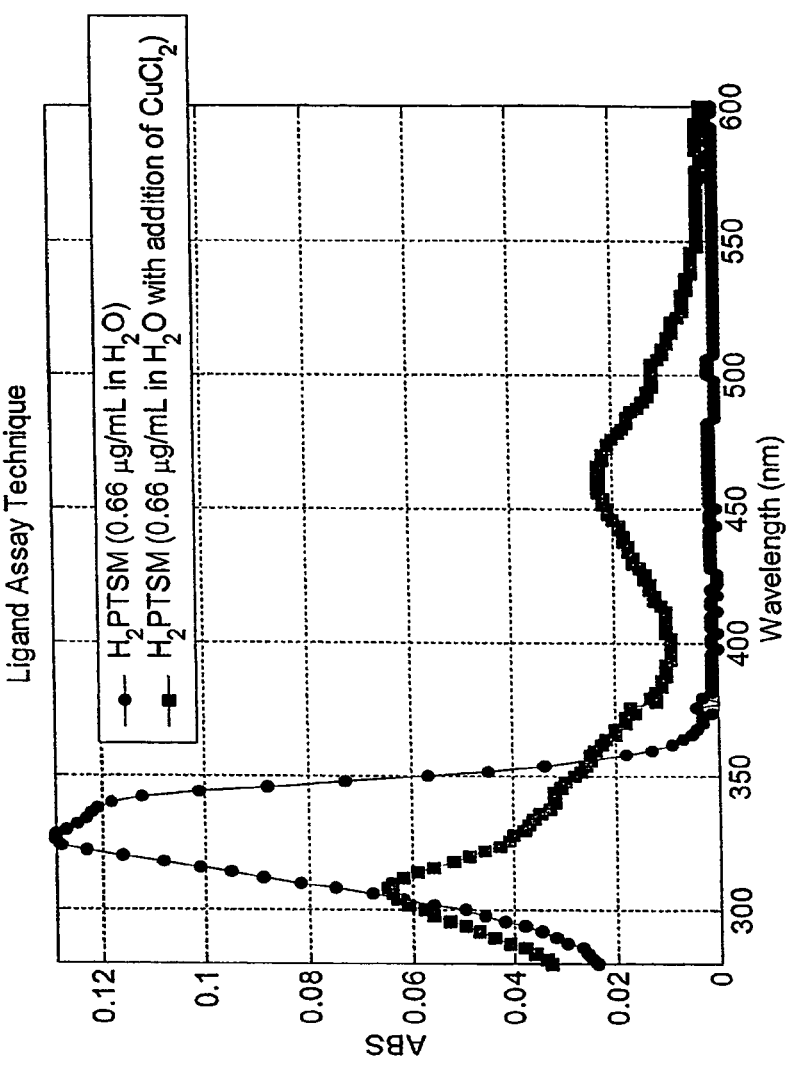
FIG. 10 shows the reference absorbance spectra for a non-lyophilized solution of $H_2PTSM$ (•) at a concentration of 0.67 µg/mL and for the Cu-PTSM (■) solution formed by addition of 0.5 µg of $CuCl_2$ to the 3 mL cuvette.
Figure 11:
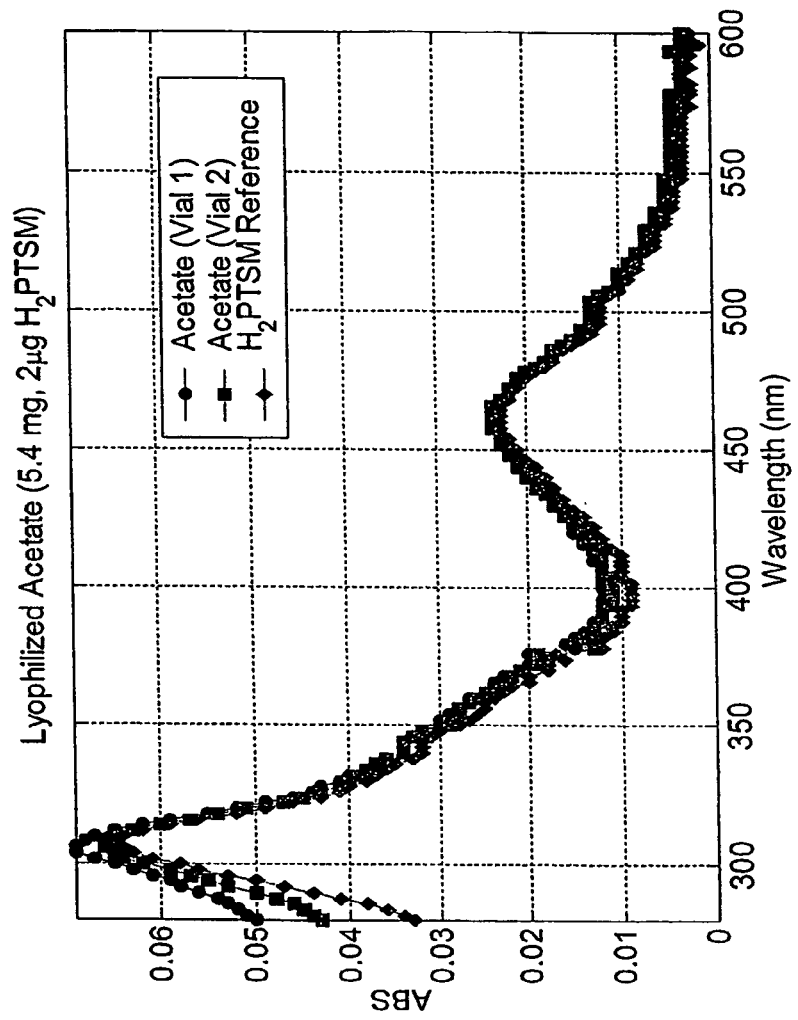
FIG. 11 shows spectra from two representative lyophilized vials for the acetate excipient.
Figure 12:
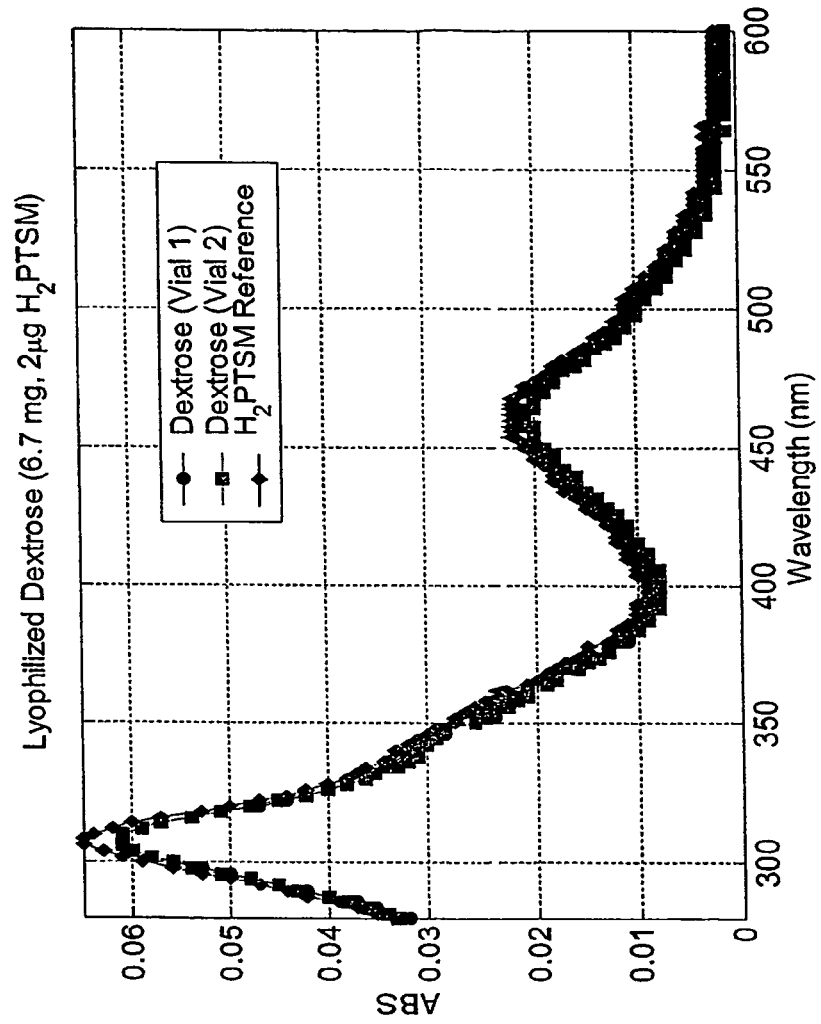
FIG. 12 shows spectra from two representative lyophilized vials for the dextrose excipient.
Figure 13:
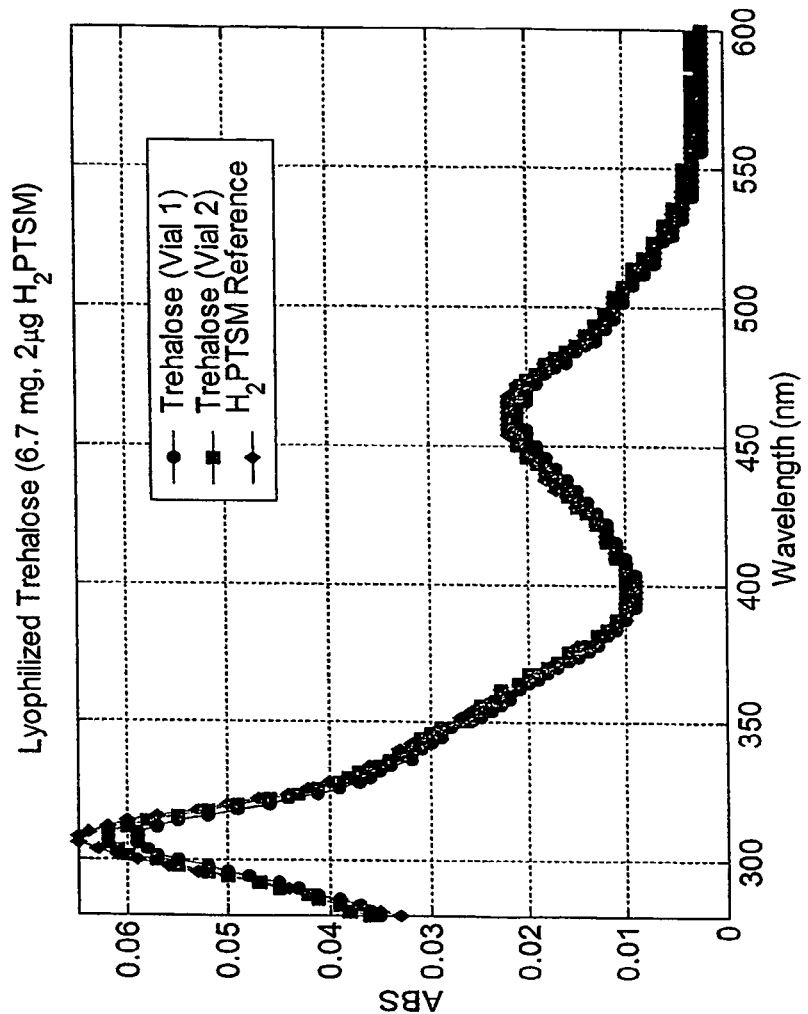
FIG. 13 shows spectra from two representative lyophilized vials for the trehalose excipient.

Using the techniques described above, lyophilized vials, containing cakes of ligand and excipient, were produced. Production was successfully accomplished using all three test excipients. Furthermore, feasibility studies of rapid reconstitution yielded exceptional results. Absorbance spectra are shown in FIG. 10-FIG. 13. FIG. 10 shows the reference absorbance spectra for a non-lyophilized solution of $H_2PTSM$ (•) at a concentration of 0.67 μg/mL and for the Cu-PTSM (■) solution formed by addition of 0.5 μg of $CuCl_2$ to the 3 mL cuvette. As may be seen in the figure, following addition of ionic copper, the $H_2PTSM$ absorbance peak (320 nm) disappears and is replaced by the characteristic absorbance peaks of Cu-PTSM (462 nm and 308 nm), demonstrating complete conversion of $H_2PTSM$ to Cu-PTSM. The effectiveness with which $H_2PTSM$ was reconstituted from the lyophilized vials may be assessed through comparison with this reference Cu-PTSM spectra. FIG. 11, FIG. 12, and FIG. 13 shows spectra from two representative lyophilized vials for the acetate, dextrose, and trehalose excipients, respectively. For comparison, each panel also includes the non-lyophilized reference Cu-PTSM spectrum from FIG. 10. As shown, for all three excipients, the spectra obtained from lyophilized ligand are virtually identical to the reference spectrum. These results show that lyophilized ligand can be completely and rapidly reconstituted.

FIG. 14 shows TLC count profiles obtained for $^{62}CuPTSM$ on C18 and silica gel media and for the ionic $^{62}Cu^{2+}$. As expected, for $^{62}CuPTSM$ profiles [see FIG. 14, (a) and (b)], a single mobile radioactive species was observed, as demonstrated by the presence of a single peak on each track. Rf values, averaged across the two tracks, were 0.49 and 0.72 for C18 and silica gel, respectively. These values agree with Rf values that have consistently been obtained for $^{62}CuPTSM$ produced using other methods. In contrast, as shown in FIG. 14(c), ionic copper remained at the origin on both media, and Rf's for ionic $^{62}Cu^{2+}$ were 0.23 and 0.19 for C18 and silica gel, respectively. The absence of an origin peak on the $^{62}CuPTSM$ profiles [FIG. 14, (a) and (b)] shows that essentially no ionic copper remained following combination with the ligand. Average radiochemical purity of $^{62}CuPTSM$, based on the TLC profiles (n=4), was 96%.

The $^{62}Zn/^{62}Cu$ microgenerator and lyophilized ligand kit can play a significant role in advancing clinical PET imaging by serving as a distribution source of a short-lived PET isotope for synthesis of a wide variety of radiopharmaceuticals. The microgenerator together with kit synthesis techniques fit seamlessly into the current regulatory and commercial paradigm of distributable radiopharmaceuticals. One center can process the bombarded target, perform necessary radiochemistry to purify the $^{62}Zn$, and load large numbers of generators. Since interchangeable kits can be employed with the same generator, the synthesis technique is both flexible and economical. The $^{62}Zn/^{62}Cu$ microgenerator and lyophilized ligand kit can play a major role in advancing clinical PET imaging in oncology, cardiology, and neurology. Finally, the miniaturization of the generator facilitates delivery and labeling in clinically convenient dose volumes.

I claim:

1. A method of producing radiopharmaceutical agents for use in positron emission tomography comprising:
   providing a column having a small volume capacity;
   filling a portion of said column with anion exchange resin beads having a small volume between 25 and 100 μl;
   introducing a $^{62}Zn$ solution into the column to bond the radioactive isotope to the beads;
   providing a septum closed vial containing lypholized ligand compound;
   soluablizing the lypholized compound in the vial by introducing a reconstitution agent;
   providing a pressurized eluant vessel in fluid communication with the column;
   releasing eluant from the eluant vessel to flow into the column and through the resin beads to a dispensing point;
   directing the eluant from the column dispensing point into the vial thereby forming a radiolabeled Cu-ligand compound.

2. The method of claim 1 wherein the compound comprises at least one bis(thiosemicarbazone) compound represented by the following formula:

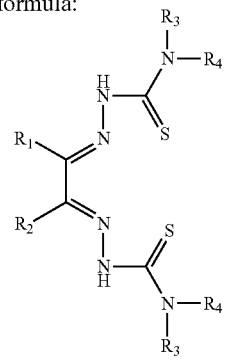

wherein $R_1$ and $R_2$ are independently hydrogen or a hydrocarbyl group; $R_3$ is hydrogen, a hydrocarbyl or an aryl group; and $R_4$ is hydrogen or a hydrocarbyl group, wherein any hydrocarbyl or aryl group optionally contains a heteroatom from the group of O, N, S, P, and Si in place of a carbon atom or a halogen atom in place of a hydrogen atom, together with a suitable excipient.

3. The method of claim 1 wherein the reconstitution agent is sterile water.

4. The method of claim 1 wherein the reconstitution agent comprises a buffering agent.

5. The method of claim 4 wherein the buffering agent is sodium acetate.

6. The method of claim 1 wherein the step of providing a lyophilized form of the ligand compound comprises
   freezing the compound;
   placing the compound under a vacuum; and
   removing the water from the compound.

7. The method of claim 1 wherein the radiolabeled Cu-ligand compound comprises a $^{62}Cu$-ligand.

8. The method of claim 7 wherein the reconstitution agent comprises 1.8M NaCl and 0.2M HCl.

9. The method of claim 7 wherein the reconstitution agent comprises a 2 molar excess of a buffer.

10. The method of claim 9 wherein the buffer is sodium acetate.

11. The method of claim 1 wherein the dispensing outlet point is a needle tip.

12. The method of claim 1 wherein for each production of a radiopharmaceutical 0.1 to 0.3 mL of eluant is released through the column at a flow rate of 100-500 μL/minute.

13. A method for producing a radiopharmaceutical comprising the steps of:
    releasing 0.1 to 0.3 mL of an eluant from an elution vessel to flow through a column containing resin beads having a $^{62}Zn$ radioactive isotope to a needle tip;
    wherein the eluant is released through the column at a flow rate of 100-500 μL/minute;

directing said eluant from the outlet point into a septum closed vial containing a water reconstituted lyophilized bis(thiosemicarbazone) compound of the formula

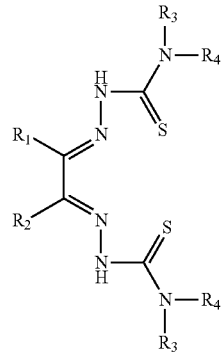

wherein $R_1$ and $R_2$ are independently hydrogen or a hydrocarbyl group; $R_3$ is hydrogen, a hydrocarbyl or an aryl group; and $R_4$ is hydrogen or a hydrocarbyl group and wherein any hydrocarbyl or aryl group optionally contains a heteroatom from the group of O, N, S, P, and Si in place of a carbon atom or a halogen atom in place of a hydrogen atom, to form an injectable solution.

14. A method for producing a radiopharmaceutical comprising the steps of:

releasing an eluant from an elution vessel to flow through a column containing resin beads having a bound radioactive isotope to a dispensing outlet point;

directing said eluant from the outlet point into a septum closed vial containing a water reconstituted lyophilized bis(thiosemicarbazone) compound of the formula

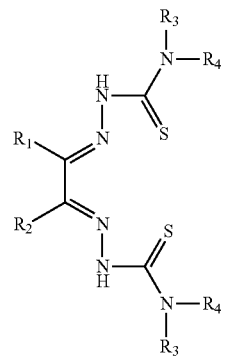

wherein $R_1$ and $R_2$ are independently hydrogen or a hydrocarbyl group; $R_3$ is hydrogen, a hydrocarbyl or an aryl group; and $R_4$ is hydrogen or a hydrocarbyl group and wherein any hydrocarbyl or aryl group optionally contains a heteroatom from the group of O, N, S, P, and Si in place of a carbon atom or a halogen atom in place of a hydrogen atom, to form an injectable solution.

15. The method of claim 14 wherein the dispensing outlet point is a needle tip.

16. The method of claim 14 wherein the bound radioactive isotope is $^{62}$Zn.

17. The method of claim 14 wherein the eluant carries $^{62}$Cu to the dispensing outlet point.

18. The method of claim 14 wherein for each production of a radiopharmaceutical 0.1 to 0.3 mL of eluant is released through the column at a flow rate of 100-500 μL/minute.

19. The method of claim 13 wherein said resin beads have a small volume between 25 and 100 μl.

20. The method of claim 14 wherein said resin beads have a small volume between 25 and 100 μl.

* * * * *